US008426467B2

(12) United States Patent
Tiwari et al.

(10) Patent No.: US 8,426,467 B2
(45) Date of Patent: Apr. 23, 2013

(54) COLORED ESMOLOL CONCENTRATE

(75) Inventors: Deepak Tiwari, Raritan, NJ (US); George Owoo, North Plainfield, NJ (US); Rekha Nayak, Monmouth Junction, NJ (US); Kenneth E. Burhop, Spring Grove, IL (US)

(73) Assignees: Baxter International Inc., Deerfield, IL (US); Baxter Healthcare SA, Glattpark (Opifkon) (CH)

( * ) Notice: Subject to any disclaimer, the term of this patent is extended or adjusted under 35 U.S.C. 154(b) by 1261 days.

(21) Appl. No.: 11/752,086

(22) Filed: May 22, 2007

(65) Prior Publication Data

US 2008/0292558 A1 Nov. 27, 2008

(51) Int. Cl.
*A01N 37/10* (2006.01)
*A01N 37/44* (2006.01)
*A61K 31/235* (2006.01)
*A61K 31/24* (2006.01)

(52) U.S. Cl.
USPC ........................................................ 514/538

(58) Field of Classification Search ............ 514/538
See application file for complete search history.

(56) References Cited

U.S. PATENT DOCUMENTS

| | | | |
|---|---|---|---|
| 2,525,071 A | 10/1950 | Hardy et al. | |
| 2,720,203 A | 10/1955 | Burns et al. | |
| 2,745,785 A | 5/1956 | Bruce et al. | |
| 3,685,261 A | 8/1972 | McIlvaine et al. | |
| 4,056,635 A | 11/1977 | Glen et al. | |
| 4,073,943 A | 2/1978 | Wretlind et al. | |
| 4,340,589 A | 7/1982 | Uemura et al. | |
| 4,387,103 A | 6/1983 | Erhardt et al. | |
| 4,452,817 A | 6/1984 | Glen et al. | |
| 4,540,602 A | 9/1985 | Motoyama et al. | |
| 4,593,119 A | 6/1986 | Erhardt et al. | |
| 4,606,939 A | 8/1986 | Frank et al. | |
| 4,606,940 A | 8/1986 | Frank et al. | |
| 4,608,278 A | 8/1986 | Frank et al. | |
| 4,622,219 A | 11/1986 | Haynes | |
| 4,725,442 A | 2/1988 | Haynes | |
| 4,786,735 A | 11/1988 | Graboyes et al. | |
| 4,798,846 A | 1/1989 | Glen et al. | |
| 4,826,689 A | 5/1989 | Violante | |
| 4,857,552 A * | 8/1989 | Rosenberg et al. ........... 514/538 |
| 4,973,465 A | 11/1990 | Baurain et al. | |
| 4,997,454 A | 3/1991 | Violante et al. | |
| 5,017,609 A | 5/1991 | Escobar et al. | |
| 5,023,271 A | 6/1991 | Vigne et al. | |
| 5,049,322 A | 9/1991 | Devissaguet et al. | |
| 5,078,994 A | 1/1992 | Nair et al. | |
| 5,091,187 A | 2/1992 | Haynes | |
| 5,091,188 A | 2/1992 | Haynes | |
| 5,100,591 A | 3/1992 | Leclef et al. | |
| 5,118,528 A | 6/1992 | Fessi et al. | |
| 5,122,543 A | 6/1992 | Khanna et al. | |
| 5,133,908 A | 7/1992 | Stainmesse et al. | |
| 5,145,684 A | 9/1992 | Liversidge et al. | |
| 5,151,264 A | 9/1992 | Samain et al. | |
| 5,152,923 A | 10/1992 | Weder et al. | |
| 5,171,566 A | 12/1992 | Mizushima et al. | |
| 5,174,930 A | 12/1992 | Stainmesse et al. | |
| 5,188,837 A | 2/1993 | Domb | |
| 5,246,707 A | 9/1993 | Haynes | |
| 5,250,236 A | 10/1993 | Gasco et al. | |
| 5,269,979 A | 12/1993 | Fountain | |
| 5,298,262 A | 3/1994 | Na et al. | |
| 5,302,401 A | 4/1994 | Liversidge et al. | |
| 5,306,519 A | 4/1994 | Peterson et al. | |
| 5,314,506 A | 5/1994 | Midler, Jr. et al. | |
| 5,318,767 A | 6/1994 | Liversidge et al. | |
| 5,326,552 A | 7/1994 | Na et al. | |
| 5,336,507 A | 8/1994 | Na et al. | |
| 5,340,564 A | 8/1994 | Illig et al. | |
| 5,346,702 A | 9/1994 | Na et al. | |
| 5,352,459 A | 10/1994 | Hollister et al. | |
| 5,354,563 A | 10/1994 | Toyotama et al. | |
| 5,389,263 A | 2/1995 | Gallagher et al. | |
| 5,399,363 A | 3/1995 | Liversidge et al. | |
| 5,417,956 A | 5/1995 | Moser | |
| 5,429,824 A | 7/1995 | June | |
| 5,447,710 A | 9/1995 | Na et al. | |
| 5,466,646 A | 11/1995 | Moser | |
| 5,468,224 A | 11/1995 | Souryal | |
| 5,470,583 A | 11/1995 | Na et al. | |
| 5,474,989 A | 12/1995 | Hashimoto et al. | |
| 5,494,683 A | 2/1996 | Liversidge et al. | |
| 5,510,118 A | 4/1996 | Bosch et al. | |

(Continued)

FOREIGN PATENT DOCUMENTS

EP 0169618 1/1986
EP 0207134 1/1987

(Continued)

OTHER PUBLICATIONS

Gurinder et al., 2002 Annual Meeting of the American Society of Anesthesiologists, Orlando, FL, USA, Oct. 12-16, 2002.*

(Continued)

*Primary Examiner* — Robert T Crow
*Assistant Examiner* — Thor Nielsen
(74) *Attorney, Agent, or Firm* — Marshall, Gerstein & Borun LLP

(57) ABSTRACT

A concentrated esmolol formulation is provided that is distinguishable from a diluted form of the concentrated esmolol formulation.

20 Claims, No Drawings

U.S. PATENT DOCUMENTS

| | | | |
|---|---|---|---|
| 5,518,187 A | 5/1996 | Bruno et al. | |
| 5,518,738 A | 5/1996 | Eickhoff et al. | |
| 5,534,270 A | 7/1996 | De Castro | |
| 5,543,133 A | 8/1996 | Swanson et al. | |
| RE35,338 E | 9/1996 | Haynes | |
| 5,552,160 A | 9/1996 | Liversidge et al. | |
| 5,560,932 A | 10/1996 | Bagchi et al. | |
| 5,560,933 A | 10/1996 | Soon-Shiong et al. | |
| 5,565,383 A | 10/1996 | Sakai et al. | |
| 5,569,448 A | 10/1996 | Wong et al. | |
| 5,573,783 A | 11/1996 | Desieno et al. | |
| 5,578,325 A | 11/1996 | Domb et al. | |
| 5,580,579 A | 12/1996 | Ruddy et al. | |
| 5,587,143 A | 12/1996 | Wong | |
| 5,591,456 A | 1/1997 | Franson et al. | |
| 5,605,785 A | 2/1997 | Texter et al. | |
| 5,626,864 A | 5/1997 | Rosenberg et al. | |
| 5,635,609 A | 6/1997 | Levy et al. | |
| 5,637,568 A | 6/1997 | Orsolini et al. | |
| 5,637,625 A | 6/1997 | Haynes | |
| 5,641,515 A | 6/1997 | Ramtoola et al. | |
| 5,641,745 A | 6/1997 | Ramtoola et al. | |
| 5,660,858 A | 8/1997 | Parikh et al. | |
| 5,662,883 A | 9/1997 | Bagchi et al. | |
| 5,662,932 A | 9/1997 | Amselem et al. | |
| 5,665,331 A | 9/1997 | Bagchi et al. | |
| 5,665,383 A | 9/1997 | Grinstaff et al. | |
| 5,679,576 A | 10/1997 | Kawai et al. | |
| 5,707,634 A | 1/1998 | Schmitt | |
| 5,716,642 A | 2/1998 | Bagchi et al. | |
| 5,720,551 A | 2/1998 | Shechter | |
| 5,766,635 A | 6/1998 | Spenleuhauer et al. | |
| 5,780,062 A | 7/1998 | Frank et al. | |
| 5,833,891 A | 11/1998 | Subramaniam et al. | |
| 5,858,410 A | 1/1999 | Muller et al. | |
| 5,862,999 A | 1/1999 | Czekai et al. | |
| 5,874,111 A | 2/1999 | Maitra et al. | |
| 5,874,574 A | 2/1999 | Johnston et al. | |
| 5,885,486 A | 3/1999 | Westesen et al. | |
| 5,885,984 A | 3/1999 | MacLeod et al. | |
| 5,886,239 A | 3/1999 | Kudzma et al. | |
| 5,916,583 A | 6/1999 | Broberg et al. | |
| 5,916,596 A | 6/1999 | Desai et al. | |
| 5,922,355 A | 7/1999 | Parikh et al. | |
| 5,939,100 A | 8/1999 | Albrechtsen et al. | |
| 5,981,719 A | 11/1999 | Woiszwillo et al. | |
| 5,989,583 A | 11/1999 | Amselem et al. | |
| 6,007,845 A | 12/1999 | Domb et al. | |
| 6,039,981 A | 3/2000 | Woo et al. | |
| 6,045,826 A | 4/2000 | Borowy-Borowski et al. | |
| 6,045,829 A | 4/2000 | Liversidge et al. | |
| 6,048,550 A | 4/2000 | Chan et al. | |
| 6,063,138 A | 5/2000 | Hanna et al. | |
| 6,063,910 A | 5/2000 | Debenedetti et al. | |
| 6,068,858 A | 5/2000 | Liversidge et al. | |
| 6,083,514 A | 7/2000 | Chang et al. | |
| 6,086,376 A | 7/2000 | Moussa et al. | |
| 6,090,925 A | 7/2000 | Woiszwillo et al. | |
| 6,090,983 A | 7/2000 | Yokoyama et al. | |
| 6,100,302 A | 8/2000 | Pejaver et al. | |
| 6,132,750 A | 10/2000 | Perrier et al. | |
| 6,139,870 A | 10/2000 | Verrecchia et al. | |
| 6,143,211 A | 11/2000 | Mathiowitz et al. | |
| 6,143,778 A | 11/2000 | Gautier et al. | |
| 6,146,663 A | 11/2000 | Bissery et al. | |
| 6,153,219 A | 11/2000 | Creeth et al. | |
| 6,153,225 A | 11/2000 | Lee et al. | |
| 6,165,506 A | 12/2000 | Jain et al. | |
| 6,177,103 B1 | 1/2001 | Pace et al. | |
| 6,197,757 B1 | 3/2001 | Perrier et al. | |
| 6,207,134 B1 | 3/2001 | Fahlvik et al. | |
| 6,207,178 B1 | 3/2001 | Westesen et al. | |
| 6,214,384 B1 | 4/2001 | Pallado et al. | |
| 6,217,886 B1 | 4/2001 | Onyuksel et al. | |
| 6,221,332 B1 | 4/2001 | Thumm et al. | |
| 6,221,398 B1 | 4/2001 | Jakupovic et al. | |
| 6,221,400 B1 | 4/2001 | Liversidge et al. | |
| 6,228,399 B1 | 5/2001 | Parikh et al. | |
| 6,231,890 B1 | 5/2001 | Naito et al. | |
| 6,235,224 B1 | 5/2001 | Mathiowitz et al. | |
| 6,238,677 B1 | 5/2001 | Fanta et al. | |
| 6,238,694 B1 | 5/2001 | Gasco et al. | |
| 6,245,349 B1 | 6/2001 | Yiv et al. | |
| 6,248,363 B1 | 6/2001 | Patel et al. | |
| 6,261,537 B1 | 7/2001 | Klaveness et al. | |
| 6,264,922 B1 | 7/2001 | Wood et al. | |
| 6,267,989 B1 | 7/2001 | Liversidge et al. | |
| 6,268,053 B1 | 7/2001 | Woiszwillo et al. | |
| 6,270,806 B1 | 8/2001 | Liversidge et al. | |
| 6,294,204 B1 | 9/2001 | Rossling et al. | |
| 6,299,906 B1 | 10/2001 | Bausch et al. | |
| 6,306,406 B1 | 10/2001 | Deluca | |
| 6,310,094 B1 | 10/2001 | Liu et al. | |
| 6,337,092 B1 | 1/2002 | Khan et al. | |
| 6,344,271 B1 | 2/2002 | Yadav et al. | |
| 6,346,533 B1 | 2/2002 | Cha et al. | |
| 6,365,191 B1 | 4/2002 | Burman et al. | |
| 6,375,986 B1 | 4/2002 | Ryde et al. | |
| 6,387,409 B1 | 5/2002 | Khan et al. | |
| 6,391,832 B2 | 5/2002 | Lyons et al. | |
| 6,395,300 B1 | 5/2002 | Straub et al. | |
| 6,428,814 B1 | 8/2002 | Bosch et al. | |
| 6,458,387 B1 | 10/2002 | Scott et al. | |
| 6,461,642 B1 | 10/2002 | Bisrat et al. | |
| 6,462,093 B1 | 10/2002 | Miyamoto et al. | |
| 6,528,540 B2 | 3/2003 | Liu et al. | |
| 6,607,784 B2 | 8/2003 | Kipp et al. | |
| 6,616,869 B2 | 9/2003 | Mathiowitz et al. | |
| 6,667,048 B1 | 12/2003 | Lambert et al. | |
| 6,682,761 B2 | 1/2004 | Pace et al. | |
| 6,835,396 B2 | 12/2004 | Brynjelsen et al. | |
| 6,869,617 B2 | 3/2005 | Kipp et al. | |
| 6,884,436 B2 | 4/2005 | Kipp et al. | |
| 7,763,469 B2* | 7/2010 | Babichenko et al. | 436/56 |
| 2001/0007678 A1 | 7/2001 | Baert et al. | |
| 2001/0025058 A1 | 9/2001 | Borowy-Borowski et al. | |
| 2001/0042932 A1 | 11/2001 | Mathiowitz et al. | |
| 2002/0012675 A1 | 1/2002 | Jain et al. | |
| 2002/0012704 A1 | 1/2002 | Pace et al. | |
| 2002/0036776 A1 | 3/2002 | Shimaoka | |
| 2002/0041896 A1 | 4/2002 | Straub et al. | |
| 2002/0048610 A1 | 4/2002 | Cima et al. | |
| 2002/0054912 A1 | 5/2002 | Kim et al. | |
| 2002/0076347 A1 | 6/2002 | Maerz | |
| 2002/0110599 A1 | 8/2002 | Auweter et al. | |
| 2002/0127278 A1 | 9/2002 | Kipp et al. | |
| 2002/0147239 A1 | 10/2002 | Liu et al. | |
| 2002/0168402 A1 | 11/2002 | Kipp et al. | |
| 2002/0182107 A1 | 12/2002 | Laugharn, Jr. et al. | |
| 2003/0003155 A1 | 1/2003 | Kipp et al. | |
| 2003/0031719 A1 | 2/2003 | Kipp et al. | |
| 2003/0044433 A1 | 3/2003 | Werling et al. | |
| 2003/0054042 A1 | 3/2003 | Liversidge et al. | |
| 2003/0059472 A1 | 3/2003 | Brynjelsen et al. | |
| 2003/0072807 A1 | 4/2003 | Wong et al. | |
| 2003/0077329 A1 | 4/2003 | Kipp et al. | |
| 2003/0096013 A1 | 5/2003 | Werling et al. | |
| 2003/0100568 A1 | 5/2003 | Werling et al. | |
| 2003/0170279 A1 | 9/2003 | Lambert et al. | |
| 2003/0206959 A9 | 11/2003 | Kipp et al. | |
| 2003/0211083 A1 | 11/2003 | Vogel et al. | |
| 2004/0022861 A1 | 2/2004 | Williams et al. | |
| 2004/0022862 A1 | 2/2004 | Kipp et al. | |
| 2004/0043077 A1 | 3/2004 | Brown | |
| 2004/0053375 A1* | 3/2004 | Tan et al. | 435/118 |
| 2004/0245662 A1 | 12/2004 | Chaubal et al. | |
| 2004/0256749 A1 | 12/2004 | Chaubal et al. | |
| 2005/0013868 A1 | 1/2005 | Brynjelsen et al. | |
| 2005/0037083 A1 | 2/2005 | Brynjelsen et al. | |
| 2005/0142375 A1* | 6/2005 | Tian et al. | 424/472 |
| 2005/0244503 A1 | 11/2005 | Rabinow et al. | |
| 2007/0141090 A1* | 6/2007 | Harris et al. | 424/400 |

FOREIGN PATENT DOCUMENTS

| | | |
|---|---|---|
| EP | 0275796 | 7/1988 |
| EP | 0349428 | 1/1990 |
| EP | 0372070 | 6/1990 |

| | | | | | |
|---|---|---|---|---|---|
| EP | 0377477 | 7/1990 | WO | WO-98/07414 | 2/1998 |
| EP | 0379379 | 7/1990 | WO | WO-98/14170 | 4/1998 |
| EP | 0423697 | 4/1991 | WO | WO-98/14174 | 4/1998 |
| EP | 0498482 | 8/1992 | WO | WO-98/14180 | 4/1998 |
| EP | 0499299 | 8/1992 | WO | WO-98/24450 | 6/1998 |
| EP | 0517565 | 12/1992 | WO | WO-98/31346 | 7/1998 |
| EP | 0535534 | 4/1993 | WO | WO-98/35666 | 8/1998 |
| EP | 0577215 | 1/1994 | WO | WO-98/47492 | 10/1998 |
| EP | 0600532 | 6/1994 | WO | WO-98/56362 | 12/1998 |
| EP | 0601618 | 6/1994 | WO | WO-98/57967 | 12/1998 |
| EP | 0601619 | 6/1994 | WO | WO-99/00113 | 1/1999 |
| EP | 0602700 | 6/1994 | WO | WO-99/02665 | 1/1999 |
| EP | 0602702 | 6/1994 | WO | WO-99/03450 | 1/1999 |
| EP | 0605024 | 7/1994 | WO | WO-99/06022 | 2/1999 |
| EP | 0642992 | 3/1995 | WO | WO-99/39696 | 2/1999 |
| EP | 0644755 | 3/1995 | WO | WO-99/16443 | 4/1999 |
| EP | 0652011 | 5/1995 | WO | WO-99/29316 | 6/1999 |
| EP | 0720471 | 7/1996 | WO | WO-99/30833 | 6/1999 |
| EP | 0730406 | 9/1996 | WO | WO-99/32156 | 7/1999 |
| EP | 0752245 | 1/1997 | WO | WO-99/33467 | 7/1999 |
| EP | 0754034 | 1/1997 | WO | WO-99/38493 | 8/1999 |
| EP | 0788350 | 8/1997 | WO | WO-99/39700 | 8/1999 |
| EP | 0804162 | 11/1997 | WO | WO-99/49846 | 10/1999 |
| EP | 0808154 | 11/1997 | WO | WO-99/49848 | 10/1999 |
| EP | 0812187 | 12/1997 | WO | WO-99/53901 | 10/1999 |
| EP | 0820300 | 1/1998 | WO | WO-99/59550 | 11/1999 |
| EP | 0828479 | 3/1998 | WO | WO-99/61001 | 12/1999 |
| EP | 0831770 | 4/1998 | WO | WO-99/65469 | 12/1999 |
| EP | 0832569 | 4/1998 | WO | WO-00/06152 | 2/2000 |
| EP | 0857484 | 8/1998 | WO | WO-00/09096 | 2/2000 |
| EP | 0988863 | 3/2000 | WO | WO-00/12124 | 3/2000 |
| EP | 1012204 | 6/2000 | WO | WO-00/12125 | 3/2000 |
| EP | 1105109 | 6/2001 | WO | WO-00/18374 | 4/2000 |
| EP | 1156788 | 11/2001 | WO | WO-00/27363 | 5/2000 |
| EP | 1210942 | 6/2002 | WO | WO-00/30615 | 6/2000 |
| EP | 1277724 | 1/2003 | WO | WO-00/30616 | 6/2000 |
| EP | 1417962 | 5/2004 | WO | WO-00/37050 | 6/2000 |
| EP | 1652533 | 5/2006 | WO | WO-00/40220 | 7/2000 |
| FR | 2817478 | 6/2002 | WO | WO-00/51572 | 9/2000 |
| FR | 2838969 | 10/2003 | WO | WO-00/59471 | 10/2000 |
| JP | 02306902 | 12/1990 | WO | WO-00/61108 | 10/2000 |
| WO | WO-85/00011 | 1/1985 | WO | WO-00/71079 | 11/2000 |
| WO | WO-86/03676 | 7/1986 | WO | WO-00/72820 | 12/2000 |
| WO | WO-89/11850 | 12/1989 | WO | WO-01/12155 | 2/2001 |
| WO | WO-89/11855 | 12/1989 | WO | WO-01/17546 | 3/2001 |
| WO | WO-90/03782 | 4/1990 | WO | WO-01/21154 | 3/2001 |
| WO | WO-90/15593 | 12/1990 | WO | WO-01/26635 | 4/2001 |
| WO | WO-91/06292 | 5/1991 | WO | WO-01/62374 | 8/2001 |
| WO | WO-91/07170 | 5/1991 | WO | WO-01/64164 | 9/2001 |
| WO | WO-91/12794 | 9/1991 | WO | WO-01/80828 | 11/2001 |
| WO | WO-91/16068 | 10/1991 | WO | WO-01/85345 | 11/2001 |
| WO | WO-92/00731 | 1/1992 | WO | WO-01/87264 | 11/2001 |
| WO | WO-92/03380 | 3/1992 | WO | WO-02/17883 | 3/2002 |
| WO | WO-92/08447 | 5/1992 | WO | WO-02/22195 | 3/2002 |
| WO | WO-92/17214 | 10/1992 | WO | WO-02/24163 | 3/2002 |
| WO | WO-93/25190 | 12/1993 | WO | WO-02/24169 | 3/2002 |
| WO | WO-94/07999 | 4/1994 | WO | WO-02/26324 | 4/2002 |
| WO | WO-94/20072 | 9/1994 | WO | WO-02/43702 | 6/2002 |
| WO | WO-95/05164 | 2/1995 | WO | WO-02/051386 | 7/2002 |
| WO | WO-95/27482 | 10/1995 | WO | WO-02/055059 | 7/2002 |
| WO | WO-95/33488 | 12/1995 | WO | WO-02/060411 | 8/2002 |
| WO | WO-96/00567 | 1/1996 | WO | WO-02/072070 | 9/2002 |
| WO | WO-96/14833 | 5/1996 | WO | WO-02/072071 | 9/2002 |
| WO | WO-96/20698 | 7/1996 | WO | WO-02/074282 | 9/2002 |
| WO | WO-96/24336 | 8/1996 | WO | WO-02/076446 | 10/2002 |
| WO | WO-96/24340 | 8/1996 | WO | WO02/076446 * | 10/2002 |
| WO | WO-96/25150 | 8/1996 | WO | WO-02/080678 | 10/2002 |
| WO | WO-96/25152 | 8/1996 | WO | WO-02/080883 | 10/2002 |
| WO | WO-96/25918 | 8/1996 | WO | WO-02/082074 | 10/2002 |
| WO | WO-96/31231 | 10/1996 | WO | WO 02/076446 A1 * | 10/2002 |
| WO | WO-97/03651 | 2/1997 | WO | WO-02/089773 | 11/2002 |
| WO | WO-97/03657 | 2/1997 | WO | WO-03/024424 | 3/2003 |
| WO | WO-97/14407 | 4/1997 | WO | WO-03/026611 | 4/2003 |
| WO | WO-97/30695 | 8/1997 | WO | WO-03/035031 | 6/2003 |
| WO | WO-97/36611 | 10/1997 | WO | WO-03/045330 | 6/2003 |
| WO | WO-97/41837 | 11/1997 | WO | WO-03/045660 | 6/2003 |
| WO | WO-97/44014 | 11/1997 | WO | WO-2004/032858 | 4/2004 |
| WO | WO-98/01162 | 1/1998 | WO | WO-2004/056666 | 7/2004 |
| WO | WO-98/07410 | 2/1998 | WO | WO-2004/075856 A2 | 9/2004 |

| WO | WO-2004/093795 | 11/2004 |
| WO | WO-2004/103348 | 12/2004 |
| WO | WO-2004/112747 | 12/2004 |

OTHER PUBLICATIONS

Akers in Remington: The Science and Practice of Pharmacy, pp. 802-804, D.B. Troy, ed., Lippincott Williams & Wilkins, pub., 2006.*
Gurinder et al., 2002 Annual Meeting of the American Society of Anesthesiologists, Orlando, FL (XP-002475538).*
Gurinder et al., "Analysis of systems failure leading to medication errors: The role of sentinel events for anesthesiologists," Anesthesiology Abstracts of Scientific Papers Annual Meeting, No. 2002, Abstract No. A-1153 (Oct. 12-16, 2002).
International Search Report and Written Opinion for international application No. PCT/US2007/075069, dated Apr. 23, 2008.
Wiest et al., "Stability of esmolol hydrochloride in 5% dextrose injection," Am. J. Health-Syst Pharm. 52:716-718 (1995).
Schaaf et al., "Stability of esmolol hydrochloride in the presence of aminophylline, bretylium tosylate, heparin sodium, and procainamide hydrochloride," Am. J. Hosp. Pharm., 47: 1567-1571 (1990).
*Summary of Color Additives Listed for Use in the United States in Food, Drugs, Cosmetics, and Medical Devices*, U.S. Food & Drug Administration/Center for Food Safety & Applied Nutrition (updated Mar. 22, 2007).
Allen et al., "Critical evaluation of acute cardiopulmonary toxicity of microspheres," J. Nucl. Med., 19:1204-1208 (1987).
Allen et al., "Effects on the murine mononuclear phagocyte system of chronic administration of liposomes containing cytotoxic drug or lipid A compared with empty liposomes," Can. J. Physiol. Pharmacol., 65:185-190 (1987).
Allen et al., "Large unilamellar liposomes with low uptake into the reticuloendothelial system," FEBS Lett., 223:42-46 (1987).
Anonymous, *Crystal Growing*. Retrieved from the Internet on Aug. 20, 2007; <URL: http://www.chem.tamu.edu/xray/pdf/guide%20to%20crystal%20growth.pdf>.
Aquaro et al., "Macrophages and HIV infection: therapeutical approaches toward this strategic virus reservoir," Antiviral Res., 55:209-225 (2002).
Avanti Polar Lipids, Inc., "Polymer and polymerizable lipids: functionalized PEG lipids," (Mar. 2003): Retrieved from the Internet : <URL: http://www.avantilipids.com>.
Avanti Polar Lipids, Inc., "Polymer and polymerizable lipids: polyethylene glycol)-lipid conjugates," (Mar. 2003). Retrieved from the Internet: <URL: http://www.avantilipids.com>.
Avanti Polar Lipids, Inc., "Synthetic products—functionalized phospholipids: lipids for conjugation of proteins/pepetides/drugs to lipsomes," (Mar. 2003). Retrieved from the Internet: <URL: http://www.avantilipids.com>.
Bender et al., "Efficiency of nanoparticles as a carrier for antiviral agents in human immunodeficiency virus-infected human monocytes/macrophases in vitro, antimicrobial agents and chemotherapy," Antimicrob. Agents Chemother., 40:1467-1471 (1996).
Crowe et al., "The contribution of monocyte infection and trafficking to viral persistence, and maintenance of the viral reservoir in HIV infection," J. Leukoc. Biol., 74:635-641 (2003).
Davis et al., "Pulmonary perfusion imaging: acute toxicity and safety factors as a function of particle size," J. Nucl. Med., 19:1209-1213 (1978).
Duncker et al., "Effects of the pharmaceutical cosolvent hydroxypropyl-beta-cyclodextrin on porcine corneal endothelium," Graefes Arch. Clin. Exp. Opthalmol., 236::380-389 (1998).
Eugen Muller (ed.), *Methoden der Organischen Chemie—Algemeine Laboratoriumspraxis*, p. 375, Stuttgart, Germany: Georg Thieme Verlag. (1958).
Fischer-Smith et al., "CNS invasion by CD14+/C016+ peripheral blood-derived monocytes in HIV dementia: perivascular accumulation and reservoir of HIV infection," J. Neurovirol., 7:528-541 (2001).
Graham et al., "The effects of freezing on commercial insulin suspensions," Int. J. Pharmaceutics, (1978).

Heiati et al., "Solid lipid nanoparticles as drug carriers: II. Plasma stability and biodistribution of solid lipid nanoparticles containing the lipophilic prodrug 3" -azido-3" -deoxythymidine palmitate in mice," Int J. Pharmaceutics, 174:71-80 (1998).
Igarashi et al., "Macrophage are the principal reservoir and sustain high virus loads in rhesus macaques after the depletion of CD4+ T cells by a highly pathogenic simian immunodeficiency virus/HIV type 1 chimera (SHIV): implications for HIV-1 infections of humans," Proc. Natl. Acad. Sci. USA, 98:658-663 (2001).
Kinman et al., "Lipid-drug association enhanced HIV-1 protease inhibitor indinavir localization in lymphoid tissues and viral load reduction: a proof of concept study in HIV-2287-infected macaques," J. Acquir. Immune Defic. Syndr., 34:387-397 (2003).
Limoges et al., "Sustained antiretroviral activity of indinavir nanosuspensions in primary monocyte-derived macrophages," poster presentation, 11th Conference on Retroviruses and Opportunistic Infections, Feb. 8-11, 2004.
Lobenberg et al., "Body distribution of azidothymidine bound to hexyl-cyanoacrylate nanoparticles after i.v. injection to rats," J. Control. Release, 50:21-30 (1998).
Lobenberg et al., "Macrophage targeting of azidothymidine: a promising strategy for AIDS therapy," AIDS Res. Hum. Retroviruses, 12:1709-1715 (1996).
Moghimi et al., "Long-circulating and target-specific nanoparticles: theory to practice," Pharmacol. Rev., 53:283-318 (2001).
Mroczka, "Integral transform technique in particle sizing," J. Aerosol Sci., 20:1075-1077 (1989).
Nesbit et al., "In vitro and animal models of human immunodeficiency virus infection of the central nervous system," Clin. Diagn. Lab. Immunol., 9:515-524 (2002).
Nottet et al., "HIV-1 entry into brain: Mechanisms for the infiltration of HIV-1-infected macrophages across the blood-brain barrier," p. 55, in Gendelman (ed.) et al., *The Neurology of AIDS*, New York: Hodder Arnold Publication (1997).
Perno et al., "Relative potency of protease inhibitors in monocytes/macrophages acutely and chronically infected with human immunodeficiency virus," J. Infect. Dis., 178:413-422 (1998).
Ricketts, *Project Habbakuk*, Retrieved from the Internet on Aug. 20, 2007, <URL: http:www.mysteriesofcanada.com/Alberta/habbakuk.htm>.
Sawchuk et al., "Investigation of distribution, transport and uptake of anti-HIV drugs to the central nervous system," Adv. Drug Deliv. Rev., 39:5-31 (1999).
Schroeder et al., "Distribution of radiolabeled subvisible microspheres after intravenous administration to beagle dogs," J. Pharm. Sci., 67:504-507 (1978).
Schroeder et al., "Physiological effects of subvisible microspheres administered intravenously to beagle dogs," J. Pharm. Sci., 67:508-513 (1978).
Shrayer et al., Ceramide, a mediator of apoptosis, synergizes with paclitaxel to induce regression of the L3.6 human pancreatic carcinoma implanted in SCID mice, J. Clin. Oncol., 22:2135 (2004).
Singla et al., "Paclitaxel and its formulations," Int. J. Pharm., 235:179-192 (2002).
Sjostrom et al., "A method for the preparation of submicron particles of sparingly water-soluble drugs by precipitation in oil-in-water emulsions. II: Influence of the emulsifier, the solvent, and the drug substance," J. Pharm. Sci., 82:584-589 (1993).
Sjostrom et al., "Preparation of submicron drug particles in lecithin-stabilized o/w emulsions I. Model studies of the precipitation of cholesteryl acetate," Int. J. Pharm., 88:53-62 (1992).
Sjostrom et al., "The formation of submicron organic particles by precipitation in an emulsion," J. Dispers. Sci. Tech., 15:89-117 (1994).
Solas et al., "Discrepancies between protease inhibitor concentrations and viral load in reservoirs and sanctuary sites in human immunodeficiency virus-infected patients," Antimicrob. Agents Chemother., 47:238-243 (2003).
Subramaniam et al., "Pharmaceutical processing with supercritical carbon dioxide," J. Pharm. Sci., 86:885-890 (1997).
Volcheck et al., "Anaphylaxis to intravenous cyclosporine and tolerance to oral cyclosporine: case report and review," Ann. Allergy Asthma Immunol., 80:159-163 (1998).

Von Briesen et al., "Controlled release of antiretroviral drugs" *AIDS Rev.*, 2:31-38 (2000).
Yokel et al., "Acute toxicity of latex microspheres," *Toxicol. Lett.*, 9:165-170 (1981).
Tiwari et al., U.S. Appl. No. 11/752,037, filed May 22, 2007.
Tiwari et al., U.S. Appl. No. 11/752,103, filed May 22, 2007.

Akers, Parenteral Preparations, Chapter 41 In: *Remington: The Science and Practice of Pharmacy*, pp. 802-804 (2006).
US 5,849,884, 12/1998, Woiszwillo et al. (withdrawn)

\* cited by examiner

US 8,426,467 B2

COLORED ESMOLOL CONCENTRATE

BACKGROUND OF THE INVENTION

The present invention is directed to colored enhanced concentrated esmolol formulations including a color additive. More specifically, the invention is directed to a concentrated esmolol formulation having a non-toxic color additive preferably approved for parenteral administration, preferably approved for I.V. administration. The invention is directed to a concentrated esmolol formulation having a color sufficient to be easily distinguishable from a dilution of the concentrate of at least a ratio of about one part concentrate to four parts diluent (1:4).

Administration of the proper dosage of a medication is one area where errors can arise. Most medications are safe and effective at the proper dosage but can have adverse consequences at high dosages. In some cases, dosing errors can have life threatening consequences.

Dosing errors can unfortunately occur with respect to liquid medications that are provided in various strengths. This is especially true where the concentrated form of the medication is visually indistinguishable from a diluted form such as with substantially clear and colorless liquids. Liquid medications can come as ready-to-use formulations and in concentrated formulations, which require dilution prior to administration. Usually the only means of differentiating between concentrated and diluted formulations is by the labeling of the container housing the medication. As an added precaution, the container itself or the closure may be given distinct attributes such as coloring. However, errors still occur because often times the medication is transferred to a secondary container such as a syringe.

In order to assist health care practitioners to identify potentially hazardous concentrated potassium chloride formulations, there have been attempts to include a color additive. One known colored, potassium chloride concentrate uses methylene blue to assist practitioners in identifying the concentrate over the diluted form. Unfortunately, due to the shortcomings of this colored concentrated potassium chloride formulation, coloring concentrated medical formulations have not been adopted with all medications in which the concentrated form can be potentially hazardous if administered directly and where the concentrated form of the medication is substantially indistinguishable from the diluted form.

There are many commonly used safe and effective liquid medications that in concentrated form could be potentially hazardous and in which the concentrate liquid is indistinguishable from a diluted form of the liquid. One widely used liquid medication that can be provided both in concentrated form and a diluted ready-to-use form is methyl-3-[4-(2-hydroxy-3-isopropylamino) propoxy]phenylpropionate hydrochloride (esmolol hydrochloride).

Esmolol (and its pharmaceutically acceptable salts, e.g., hydrochloride salt) and related compounds have β-adrenergic blocking activity. β-blockers are therapeutically effective agents for the treatment and prophylaxis of cardiac disorders when administered in the appropriate dosage. However, high doses can cause dangerously low cardiac output. Esmolol, which is a short-acting β-blocker, is often times used in acute care settings to control the heart rate of a patient. Ready-to-use isotonic and concentrated formulations of esmolol hydrochloride and related compounds are disclosed in U.S. Pat. Nos. 5,017,609, 6,310,094, and 6,528,540, incorporated herein by reference. Methods for making esmolol and related compounds and methods for treatment or prophylaxis of cardiac disorders using such compounds are disclosed in U.S. Pat. Nos. 4,387,103 and 4,593,119, incorporated herein by reference.

Since esmolol formulations are substantially clear and colorless, the concentrated formulation is visually indistinguishable from a diluted formulation. Since esmolol hydrochloride can be provided as either a concentrate or in ready-to-use strength, it is desirable to have some means of identifying the concentrate once it has been removed from its primary container.

It would be desirable to provide a concentrated esmolol formulation that is readily distinguishable from a dilution of the colored concentrate.

SUMMARY OF THE INVENTION

In one aspect of the present invention, a colored concentrated esmolol formulation is provided. The colored concentrated esmolol formulation comprises from about 25 to about 1000 mg/ml of esmolol (or pharmaceutically acceptable salts thereof), from about 0.005 to about 2 M of a buffering agent, pH adjusted to between about 3.5 and about 7.0, and a color additive.

In another aspect of the present invention a medical product is provided. The medical product comprises a concentrated esmolol formulation including from about 25 to about 1000 mg/ml of esmolol (or a pharmaceutically acceptable salt thereof) and a color additive, instructions, and a package housing the colored concentrated esmolol formulation and instructions.

In yet another aspect of the present invention a method of distinguishing a concentrated esmolol formulation is provided. The method comprises the steps of providing a colored concentrated esmolol formulation including from about 25 to about 1000 mg/ml of esmolol (or a pharmaceutically acceptable salt thereof) and a color additive.

DETAILED DESCRIPTION OF THE INVENTION

In one embodiment of the present invention, a concentrated esmolol formulation is provided that is colored to permit identification of the concentrate, to be distinguishable from a dilution of the colored concentrate and to be distinguishable from other ready-to-use esmolol formulations. The colored concentrate is suitable for parental administration once diluted to the proper concentration.

The colored esmolol concentrate includes esmolol, or pharmaceutically acceptable salts thereof, e.g., hydrochloride, and a coloring agent in an aqueous solution. As used herein, "esmolol" refers to esmolol free base and pharmaceutically acceptable salts. The solution is preferably packaged in a suitable container and terminally sterilized by autoclaving. Alternatively, the colored esmolol concentrate can be prepared by aseptic fill procedures. The concentration of esmolol hydrochloride in the colored esmolol concentrate can be from about 25 to about 1000 mg/ml. Preferably, the esmolol concentration in the concentrate formulation ranges from about 50 to 500 mg/ml, more preferably from about 100 to 300 mg/ml, and most preferably of about 250 mg/ml.

The colored concentrate may also include a pharmaceutically acceptable buffer to maintain the pH in a range of from about 3.5 to about 7.0. Preferably, the pH is maintained between about 4.5 and about 5.5, more preferably between 4.9 and 5.1. Degradation of esmolol occurs most rapidly when the pH is outside the range of 4.0 to 6.0 and is most stable around a pH of about 5.0.

Suitable buffers are those buffers that provide sufficient buffering capacity at the desired pH range and are pharmaceutically acceptable for injection into a patient. Examples of buffers useful in the present invention include, but are not limited to, acetate, glutamate, citrate, tartrate, benzoate, lactate, gluconate, phosphate and glycine and conjugate acids thereof. The concentration of the buffer can be from about 0.005 molar (M) to about 2 M. In a preferred embodiment the buffering agent comprises a combination of sodium acetate and glacial acetic acid. A preferred combination of buffers can include sodium acetate at from about 0.005 to about 0.3 M and glacial acetic acid at from about 0.05 to about 0.3 M.

To improve the stability of the colored concentrate, one or more alcohols can be included. The one or more alcohols may be included at a concentration of from about 1 to about 60% by volume, depending on the alcohol or mixture of alcohols. A preferred alcohol is ethanol, preferably included at a concentration of from about 5 to about 60% by volume, more preferably from about 10 to about 45% by volume and more preferably from about 20 to about 30% by volume. Another preferred alcohol is benzyl alcohol preferably included at a concentration of from about 1 to about 20% by volume.

For enhancing the stability of esmolol the colored esmolol concentrate can also contain a physiologically acceptable liquid polyhydric compound, preferably at a concentration of from about 5 to about 60% by volume, more preferably from about 10 to about 45% by volume and even more preferably from about 20 to about 30% by volume. Physiologically acceptable liquid polyhydric compounds include, but are not limited to, alkyls of from 1 to about 10 carbon atoms having two or more adjacent hydroxyl groups such as ethylene glycol, propylene glycol, glycerol and the like; polyethyleneglycols having a molecular weight of from about 200 to about 600 daltons; and glycerin. Preferred liquid polyhydric compounds include alkyls of from 1 to about 10 carbon atoms having two or more adjacent hydroxyl groups, and polyethyleneglycols having a molecular weight of from about 200 to about 600 daltons. A preferred liquid polyhydric compound is propylene glycol. In a preferred embodiment liquid polyhydric compounds, in conjunction with ethanol are useful in stabilizing the concentrated esmolol solutions. A preferred combination includes ethanol and propylene glycol. In a preferred composition, the volume ratio of ethanol to the propylene glycol can be about 1:1. In another preferred embodiment the concentration of ethanol is from about 20 to about 30% by volume, preferably about 26.5% by volume and the concentration of propylene glycol is from about 20 to about 30% by volume preferably about 25% by volume.

The colored concentrate includes one or more non-toxic or relatively non-toxic color additives. The color additives or agents used in the present invention are preferably approved for parenteral administration including intravenous administration. Color agents include, but are not limited to, cyanocobalamin, indigo carmine, patent blue, indocyanine green, phenopheylene, and hemoglobin. The United States Food and Drug Administration has published and has listed at its website, www.cfsan.fda.gov/~dms/opa-col2.html or successor website, incorporated herein by reference, a series of colorants that have been used in foods, drugs and medical devices. It should be noted that not all of these color additives have been approved for parenteral use in all countries. A preferred set of colorants that maybe useful in the present invention include the vitamin-based agents, including, but not limited to, Vitamin B12 (cyanocobalamin—pink in color). Vitamin B2 (riboflavin—orange in color). Other preferred colorants can include naturally occurring mineral based colorants. The colorants listed and including those listed at the FDA website may be useful in the present invention so long as the colorants provide sufficient differentiating color, versus a clear solution, and are pharmaceutically acceptable for parenteral administration to a subject.

The amount of color additive is highly dependent on the specific coloring agent selected. The coloring agent should be added in an amount sufficient to clearly distinguish the colored esmolol concentrate from a diluted formulation containing esmolol. Esmolol solutions are substantially clear and colorless even with the addition of the buffering agent or alcohol such as ethanol and propylene glycol in the concentrations disclosed above. In addition, an amount of the coloring agent should be added such that a dilution of at least about 1:4 of the colored esmolol concentrate produces a diluted esmolol formulation that is preferably more similar in color to an uncolored esmolol concentrate, i.e. substantially clear and colorless or the color of the diluent, than to the starting colored concentrate.

In one embodiment, cyanocobalamin is included as the coloring agent of the colored esmolol concentrate at a concentration of from about 0.002 to about 0.003 mg/ml, preferably 0.0024 mg/ml. At such a concentration, the otherwise clear colorless esmolol solution is given a light pink color. When diluted at a ratio of at least 1:4 with a diluent suitable for parenteral administration such as Ringer's solution or I.V., the resulting solution is at least substantially colorless or the color of the diluent.

In another embodiment, indigo carmine is included as the coloring agent of the colored esmolol concentrate at a concentration of from about 0.0005 to about 0.001 mg/ml, preferably 0.0008 mg/ml. At such a concentration, the otherwise clear colorless esmolol concentrated solution is given a light blue color. When diluted at a ratio of at least 1:4 with a diluent suitable for parenteral administration such as Ringer's solution or I.V., the resulting solution is almost colorless or the color of the diluent.

In another embodiment, patent blue is included as the coloring agent of the colored esmolol concentrate at a concentration of from about 0.0001 to about 0.0003 mg/ml, preferably 0.0002 mg/ml. At such a concentration, the otherwise clear colorless esmolol concentrated solution is given a light blue color. When diluted at a ratio of at least 1:4 with a diluent suitable for parenteral administration such as Ringer's solution or I.V., the resulting solution is at least substantially colorless or the color of the diluent.

The colored esmolol concentrate can be diluted by isotonic solutions such as Ringers' or other diluents used in the art, or with water for injection to allow parenteral administration to a patient. For example, the diluted composition may be administered in the form of a bolus injection or intravenous infusion. Suitable routes for parenteral administration include intravenous, subcutaneous, intradermal, intramuscular, intraarticular and intrathecal. The diluted concentrate is preferably administered by intravenous infusion.

Suitable containers for housing the colored esmolol concentrate are known in the art. They include vial, syringe, bag, bottle and ampul presentations and should be transparent or have a transparent portion to permit visually identification of the color. Containers may be fabricated of polymeric materials or from glass. Preferred polymeric containers are free of polyvinychlorine (PVC). Preferably the container has excellent barrier properties. A preferred container retains a moisture barrier such as glass containers or polymeric containers including barrier layers or secondary packaging. An aluminum overpouch is a preferred moisture barrier for use as secondary packaging for polymeric containers lacking a moisture barrier of their own.

Preferred containers should be able to withstand terminal sterilization such as autoclaving. Alternatively, the colored concentrate can be aseptically prepared or terminally sterilized via autoclaving separately and then placed in sterile containers using aseptic procedure. Typical autoclave cycles used in the pharmaceutical industry to achieve terminal sterilization of the final product are 121° C. for 15 minutes. The colored esmolol concentrate of the present invention can be autoclaved at a temperature ranging from 115 to 130° C. for a period of time ranging from 5 to 40 minutes with acceptable stability. Autoclaving is preferably carried out in the temperature range of 119 to 122° C. for a period of time ranging from 10 to 36 minutes.

In one embodiment the colored concentrate is housed in a clear glass or polymer based syringe and terminally sterilized. These pre-filled syringes can be provided in various volumes to permit quick and easy preparation of either small volume or large volume parenteral dosage by dispensing the contents of the pre-filled syringes into standard pre-filled intravenous fluid bags. This would eliminate the risk of miscalculating the proper dilution. In another embodiment, the pre-filled syringe houses a colored esmolol concentrate having an esmolol concentration of about 25 to 1000 mg/ml.

In another embodiment of the present invention, a medical product includes a container housing a colored esmolol concentrate and instructions kept together in a single package. The container is clear and colorless or at least includes a portion that is clear and colorless. The instructions can inform the practitioner that a color additive has been added to indicate a concentrated formulation. The instructions can also provide either a description or a representation of the color of the undiluted colored esmolol concentrate or the colored concentrate after the recommended dilution or dilutions.

In yet another embodiment of the present invention, a method of allowing identification of a concentrated esmolol formulation is provided. The method can include the step of providing a colored concentrated esmolol formulation. The colored concentrated esmolol can include from about 25 to about 1000 mg/ml of esmolol and a color additive.

The following examples further illustrate the invention but, should not be construed as in any way limiting its scope.

EXAMPLE 1

The following describes the preparation of a colored esmolol concentrate containing 250 mg/mL of esmolol HCl and a colorant after compounding, packaging and autoclave sterilization. The concentration of each ingredient of the composition is provided in Table 1 as follows:

TABLE 1

| Ingredient | Concentration |
| --- | --- |
| Esmolol HCl | 250 mg/mL |
| Sodium Acetate Trihydrate | 17 mg/mL |
| Glacial Acetic Acid | 0.00715 mL/mL |
| Alcohol, USP | 0.265 mL/mL |
| Propylene Glycol, USP | 0.25 mL/mL |
| Cyanocobalamine | 0.0024 mg/mL |
| Water for Injection, USP | QS |

The equipment and glassware for compounding, filtering, and filling are properly washed and depyrogenated. The filter assembly, filling tube assembly, and other parts and equipment are sterilized.

Eighty percent (80%) of the final volume of cool water for injection is collected in a compounding tank. Glacial acetic acid and sodium acetate are then added to the tank. Esmolol Hydrochloride is weighed and added to the tank. Propylene glycol and ethanol are weighed and added to the tank. Required quantity of the colorant is weighed and added to the tank. The solution is stirred until all excipients are dissolved. The solution is then adjusted to pH 5.0 with 1.0N sodium hydroxide or hydrochloric acid. The solution is brought to final volume with water for injection and mixed. The colored esmolol concentrate is transferred to a container and autoclaved to provide an esmolol hydrochloride solution having a concentration of about 250 mg/ml.

The color is light pink and after 1:4 dilution of with water. The resulting 50 mg/ml esmolol solution is clear and colorless and has a concentration of about 0.00048 mg/ml cyanocobalamine.

EXAMPLE 2

The following describes the preparation of a colored esmolol concentrate containing 250 mg/mL of esmolol HCl and a colorant after compounding, packaging and autoclave sterilization. The concentration of each ingredient of the composition is provided in Table 2 as follows:

TABLE 2

| Ingredient | Concentration |
| --- | --- |
| Esmolol HCL | 250 mg/mL |
| Sodium Acetate Trihydrate | 17 mg/mL |
| Glacial Acetic Acid | 0.00715 mL/mL |
| Alcohol, USP | 0.265 mL/mL |
| Propylene Glycol, USP | 0.25 mL/mL |
| Patent Blue | 0.0002 mg/mL |
| Water for Injection, USP | Qs |

The formulation of Table 2 was made similarly to the formulation of Example 1, with the exception of the different colorant and concentration.

The color is light blue and after 1:4 dilution of with water. The resulting 50 mg/ml esmolol solution is clear and colorless and has a concentration of about 0.000004 mg/ml patent blue.

EXAMPLE 3

The following describes the preparation of a colored esmolol concentrate containing 250 mg/mL of esmolol HCl and a colorant after compounding, packaging and autoclave sterilization. The concentration of each ingredient of the composition is provided in Table 3 as follows:

TABLE 3

| Ingredient | Concentration |
| --- | --- |
| Esmolol HCL | 250 mg/mL |
| Sodium Acetate Trihydrate | 17 mg/mL |
| Glacial Acetic Acid | 0.00715 mL/mL |
| Alcohol, USP | 0.265 mL/mL |
| Propylene Glycol, USP | 0.25 mL/mL |
| Indigo Carmine | 0.0008 mg/mL |
| Water for Injection, USP | Qs |

The formulation of Table 3 was made similarly to the formulation of Example 1, with the exception of the different colorant and concentration.

EXAMPLE 4

The following describes the preparation of an esmolol concentrate containing from 25-1000 mg/mL of Esmolol HCL and benzyl alcohol. The concentration of each ingredient of the composition is as follows:

TABLE 4

| Ingredient | Concentration |
| --- | --- |
| Esmolol HCL | 25-1000 mg/mL |
| Sodium Acetate Trihydrate | 17 mg/mL |
| Glacial Acetic Acid | 0.00715 mL/mL |
| Benzyl Alcohol, USP | 1-10% |
| Water for Injection, USP | Qs |

The equipment and glassware for compounding, filtering, and filling are properly washed and depyrogenated. The filter assembly, filling tube assembly, and other parts and equipment are sterilized.

Eighty percent (80%) of the final volume of cool water for injection is collected in a compounding tank. Glacial acetic acid and sodium acetate are then added to the tank. Esmolol hydrochloride is weighed and added to the tank. Required quantity of the benzyl alcohol is weighed and added to the tank. The solution is stirred until all excipients are dissolved. The solution is then adjusted to pH 5.0 with 1.0N sodium hydroxide or hydrochloric acid. The solution is brought to final volume with water for injection and mixed.

Although the present invention has been described by reference to certain preferred embodiments, it should be understood that the preferred embodiments are merely illustrative of the principles of the present invention. Therefore, modifications and/or changes may be made by those skilled in the art without departing from the true spirit and scope of the invention as defined by the appended claims.

The invention claimed is:

1. A colored concentrated esmolol formulation comprising:
   a) from about 25 to about 1000 mg/ml of esmolol;
   b) from about 0.005 to about 2 M of a buffering agent; and
   c) a color additive selected from the group consisting of indocyanine green, phenolpthalein, hemoglobin, cyanocobalamin, patent blue, indigo carmine, vitamin B2 and naturally occurring vitamins and minerals;
   wherein the formulation has a pH of from about 3.5 to about 7.0, and wherein the concentrated esmolol formulation has a color which is distinguishable from a dilution of the concentrated esmolol formulation, the dilution having a ratio of about one part concentrate to at least four parts diluent.

2. The formulation of claim 1, wherein the buffering agent comprises at least one of acetate, glutamate, citrate, tartrate, benzoate, lactate, gluconate, phosphate and glycine and conjugate acids thereof.

3. The formulation of claim 2, wherein the buffering agent comprises sodium acetate and acetic acid.

4. The formulation of claim 3 further comprising from about 1 to about 60% by volume ethanol and from about 5 to about 60% by volume propylene glycol.

5. The formulation of claim 4 comprising about 26.5% by volume ethanol and 25% by volume propylene glycol.

6. The formulation of claim 1, wherein the coloring agent is cyanocobalamin.

7. The formulation of claim 1 wherein the coloring agent is selected from the group consisting of from about 0.002 to about 0.003 mg/ml of cyanocobalamin, from about 0.0005 to about 0.001 mg/ml of indigo carmine and from about 0.0001 to about 0.0003 mg/ml of patent blue.

8. The formulation of claim 1 comprising:
   a) about 250 mg/ml esmolol HCl;
   b) about 17 mg/ml sodium acetate trihydrate;
   c) about 0.00715 ml/ml glacial acetic acid;
   d) about 0.265 ml/ml ethanol;
   e) about 0.25 ml/ml propylene glycol; and
   f) about 0.0024 mg/ml cyanocobalamin.

9. The formulation of claim 1 comprising:
   a) about 250 mg/ml esmolol HCl;
   b) about 17 mg/ml sodium acetate trihydrate;
   c) about 0.00715 ml/ml glacial acetic acid;
   d) about 0.265 ml/ml ethanol;
   e) about 0.25 ml/ml propylene glycol; and
   f) about 0.0002 mg/ml patent blue.

10. The formulation of claim 1 comprising:
    a) about 250 mg/ml esmolol HCl;
    b) about 17 mg/ml sodium acetate trihydrate;
    c) about 0.00715 ml/ml glacial acetic acid;
    d) about 0.265 ml/ml ethanol;
    e) about 0.25 ml/ml propylene glycol; and
    f) about 0.0008 mg/ml indigo carmine.

11. The colored concentrated esmolol formulation of claim 1, wherein the formulation comprises from about 100 to 300 mg/ml of esmolol.

12. The colored concentrated esmolol formulation of claim 1, wherein the dilution of the concentrated esmolol formulation is substantially colorless or the color of the diluent.

13. A medical product comprising:
    a) a concentrated esmolol formulation comprising from about 25 to about 1000 mg/ml of esmolol hydrochloride, about 0.005 to about 2 M of a buffering agent and a color additive selected from the group consisting of indocyanine green, phenolpthalein, hemoglobin, cyanocobalamin, patent blue, indigo carmine, vitamin B2 and naturally occurring vitamins and minerals housed in a container, wherein the concentrated esmolol formulation has a color which is distinguishable from a dilution of the concentrated esmolol formulation, the dilution having a ratio of about one part concentrate to at least four parts diluent.
    b) instructions; and
    c) a package housing the container and instructions.

14. The medical product of claim 13, wherein the buffering agent comprises at least one of acetate, glutamate, citrate, tartrate, benzoate, lactate, gluconate, phosphate and glycine and conjugate acids thereof.

15. The medical product of claim 14, wherein the buffering agent comprises sodium acetate and acetic acid.

16. The medical product of claim 15 further comprising from about 5 to about 60% by volume ethanol and from about 5 to about 60% by volume propylene glycol.

17. The medical product of claim 16 comprising about 26.5% by volume ethanol and 25% by volume propylene glycol.

18. The medical product of claim 13 wherein the color additive is selected from the group consisting of from about 0.002 to about 0.003 mg/ml of cyanocobalamin, from about 0.0005 to about 0.001 mg/ml of indigo carmine and from about 0.0001 to about 0.0003 mg/ml of patent blue.

19. The medical product of claim 13, wherein the formulation comprises:
    a) about 250 mg/ml esmolol HCl;
    b) about 17mg/ml sodium acetate trihydrate;
    c) about 0.00715 ml/ml glacial acetic acid;
    d) about 0.265 ml/ml ethanol;
    e) about 0.25 ml/ml propylene glycol; and f) a color additive and amount selected from the group consisting of about 0.0008 mg/ml indigo carmine, about 0.0002 mg/ml patent blue, about 0.0024 mg/ml cyanocobalamin.

20. The medical product of claim 13 wherein the instructions notify that a color additive has been added to the concentrated esmolol formulation. diluent.

* * * * *

UNITED STATES PATENT AND TRADEMARK OFFICE
CERTIFICATE OF CORRECTION

PATENT NO. : 8,426,467 B2
APPLICATION NO. : 11/752086
DATED : April 23, 2013
INVENTOR(S) : Deepak Tiwari It is certified that error appears in the above-identified patent and that said Letters Patent is hereby corrected as shown below:

In the Claims:

At Column 9, line 7, "formulation. diluent." should be -- formulation --.

Signed and Sealed this
Second Day of July, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,426,467 B2 | Page 1 of 1 |
| APPLICATION NO. | : 11/752086 | |
| DATED | : April 23, 2013 | |
| INVENTOR(S) | : Tiwari et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1378 days.

Signed and Sealed this
Second Day of December, 2014

Michelle K. Lee
*Deputy Director of the United States Patent and Trademark Office*